(12) United States Patent
Yang et al.

(10) Patent No.: US 8,226,981 B2
(45) Date of Patent: Jul. 24, 2012

(54) METHOD OF PREPARING A TASTE-MASKING ORAL DOSAGE FORM

(75) Inventors: Chih-Chiang Yang, Taipei (TW); Wen-Che Wang, Danshuei Township, Taipei County (TW); Hui-Yu Chen, Banciao (TW)

(73) Assignee: Medical and Pharmaceutical Industry Technology and Development Center, Taipei (TW)

( * ) Notice: Subject to any disclaimer, the term of this patent is extended or adjusted under 35 U.S.C. 154(b) by 515 days.

(21) Appl. No.: 11/896,753

(22) Filed: Sep. 5, 2007

(65) Prior Publication Data

US 2008/0003297 A1   Jan. 3, 2008

Related U.S. Application Data

(62) Division of application No. 10/839,243, filed on May 6, 2004, now abandoned.

(30) Foreign Application Priority Data

Feb. 25, 2004 (TW) .............................. 93104745 A

(51) Int. Cl.
*A61K 9/20* (2006.01)
*A61K 9/26* (2006.01)
*A61K 9/46* (2006.01)

(52) U.S. Cl. ......... 424/466; 424/464; 424/469; 424/470

(58) Field of Classification Search .................. 424/434, 424/64, 465, 466, 468, 489; *A61K 9/14, A61K 9/20, 9/26*
See application file for complete search history.

(56) References Cited

U.S. PATENT DOCUMENTS

| | | | |
|---|---|---|---|
| 4,940,588 A | | 7/1990 | Sparks et al. |
| 5,082,667 A | * | 1/1992 | Van Scoik ..................... 424/469 |
| 5,160,745 A | | 11/1992 | DeLuca et al. |
| 5,178,878 A | | 1/1993 | Wehling et al. |
| 5,501,861 A | * | 3/1996 | Makino et al. ................. 424/464 |
| 5,607,697 A | | 3/1997 | Alkire et al. |
| 5,804,212 A | | 9/1998 | Illum |
| 6,024,981 A | * | 2/2000 | Khankari et al. ............. 424/464 |
| 6,570,036 B1 | | 5/2003 | Reuter |
| 6,601,861 B1 | * | 8/2003 | Dettmann et al. ......... 280/47.35 |
| 2003/0180352 A1 | | 9/2003 | Patel et al. |
| 2003/0206959 A9 | * | 11/2003 | Kipp et al. ..................... 424/489 |

FOREIGN PATENT DOCUMENTS

| | | |
|---|---|---|
| CN | 561057 | 11/2003 |
| CN | I271198 | 1/2007 |
| EP | 0 230 264 A2 | 1/1987 |
| EP | 0 230 264 B1 | 1/1987 |
| TW | 561057 | 11/2003 |
| TW | I271198 | 1/2007 |

OTHER PUBLICATIONS

Handbook of Pharmaceutical Excipients, American Pharmaceutical Association (1986), p. 165.*
Desiraju, Gautam R., "Crystal and Co-crystal", CrystEngComm, 2003, 5(82), 466-467.*
Online Etymology Dictionary: "polyhedron" (http://www.etymonline.com/index.php?term=polyhedron); Mar. 18, 2011.
Itiola et al., "Tableting Characteristics of Metronidazole Formulations," International Journal of Pharmaceutics 31:99-105 (1986).
Sugimoto et al., "The Preparation of Rapidly Disintegrating Tablets in the Mouth," Pharmaceutical Development and Technology, 6(4):487-493 (2001).
Remington, The Science and Practice of Pharmacy, vol. II, pp. 392, 1616-1620, 1624, 1627-1629, 1635-1637, The Philadelphia College of Pharmacy and Science (1995).

* cited by examiner

*Primary Examiner* — Robert A Wax
*Assistant Examiner* — Jeffrey T Palenik
(74) *Attorney, Agent, or Firm* — Occhiuti Rohlicek & Tsao LLP

(57) ABSTRACT

A method of preparing a taste-masking oral dosage form is provided. The method includes providing a first solution comprising a pharmaceutically active ingredient and a starch, providing a second solution comprising a hydrophilic polymer and a surfactant, blending the first and second solution to form a plurality of microparticles by a granulating process, wherein the microparticle is a co-crystal structure comprising the pharmaceutically active ingredient and the starch, and performing a compression-molding process to form the tablet.

18 Claims, 3 Drawing Sheets

METHOD OF PREPARING A TASTE-MASKING ORAL DOSAGE FORM

RELATED APPLICATION

This Application is a Divisional Application of U.S. patent application Ser. No. 10/839,243, filed on May 6, 2004 now abandoned, which claims the priority of Taiwan Application No. 93104745, filed on Feb. 25, 2004, which are incorporated herein by references.

BACKGROUND OF THE INVENTION

1. Field of the Invention

The present invention relates to a pharmaceutical composition, and more specifically to a taste-masking oral dosage form and method of preparing the same.

2. Description of the Related Art

There are various types of oral administrative medicines, such as tablets, capsules, granules, powders, syrups and the like. Orally administrated medicines, however, suffer from many drawbacks. For example, pharmaceutically active ingredients in medicines may leave an unpleasant taste after drug administration.

Tablets and capsules, for example, may be hard to swallow for the elderly or children. Granules and powders may possibly enter the respiratory tract or lungs. Additionally, dosage of syrups, may be difficult measured, particularly for the elderly or children.

Therefore, many researches regarding taste-masking oral dosage forms have been undertaken recently to provide a new generation rapidly dissolved and safely swallowed tablets, and their dosages can be accurately measured, particularly can mask bitter. Additionally, tablets should possess adequate hardness to facilitate the packaging process.

Several related arts are disclosed in the following. U.S. Pat. No. 5,804,212 describes a preparation in which a starch and a nasal drug are blended to form a microparticle to improve nasal absorption. European Patent No. 230264 discloses an aqueous nasal drug delivery system for vaccines comprising a high molecular weight drug, a gelling agent such as hydroxyethyl cellulose, and additives such as surfactants or glycerol. The two examples (U.S. Pat. No. 5,804,212 and European Patent No. 230264) merely cite how to improve drug absorption effects, without commenting on taste-masking effects.

Japanese Patent Laid-open No. 76420/1977 and 24410/1983 describe a method of preparing a porous tablet which comprises blending a tablet-constituting composition with inert solvent, solidifying, compressing the resulting solid into tablets, and evaporating solvent by freeze-drying. U.S. Pat. No. 5,501,861 discloses a method of preparing a fast dissolving tablet comprising a water-soluble saccharide (such as sugar, starch, lactose, sugar alcohol, or tetrose) and a pharmacologically active ingredient, which comprises compressing the blended solid into tablets with a molding pressure of 5~130 kg/cm$^2$ and evaporating the solvent by freeze-drying.

The above fast dissolving tablets are prepared by Zydis (from R. P. Scherer, England) freeze-drying. This method, however, suffer from high process cost and insufficient mechanical strength of the preparation.

Therefore, it is necessary to develop a preparation which offers a pleasant taste and acceptable disintegration speed in an oral cavity after dosage, and possesses a sufficient mechanical strength so as to protect the preparation from destruction in the course of manufacture.

SUMMARY OF THE INVENTION

In order to solve the conventional problems, an object of the invention is to provide an oral dosage form having taste-masking effects, rapid disintegration rates, sufficient hardness to resist destruction during the course of manufacture and storage, and low cost.

To achieve the above objects, the invention provides a taste-masking oral dosage form comprising a pharmaceutically active ingredient, and a starch, wherein the pharmaceutically active ingredient is packaged by the starch to form a microparticle. The tablet further comprises a hydrophilic polymer, a surfactant, excipicents, or combinations thereof.

The tablet provided in the invention may be rapidly dissolved in an oral cavity, due to the hydrophilic polymer having strong water absorption, so that it can be advantageously used for treatment of diseases in the elderly or children. Additionally, the dissolution rate of the tablet is improved by the surfactant in an oral cavity, particularly for very slightly dissolved drugs.

Another object of the invention is to provide a method of preparing a taste-masking oral dosage form, comprising the following steps. A first solution comprising a pharmaceutically active ingredient and a starch is provided. A second solution comprising a hydrophilic polymer and a surfactant is then provided. Subsequently, the first and second solutions are blended to form a plurality of microparticles by a granulating, and a compression-molding process is performed to form the tablet.

The tablet has an adequate hardness and rapid dissolving rate, due to the specific granulation and additives thereof. More particularly, the bitter taste is wasted, because the pharmaceutically active ingredient is packaged by the starch. Additionally, the low-cost compression-molding process satisfies industry requirements.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
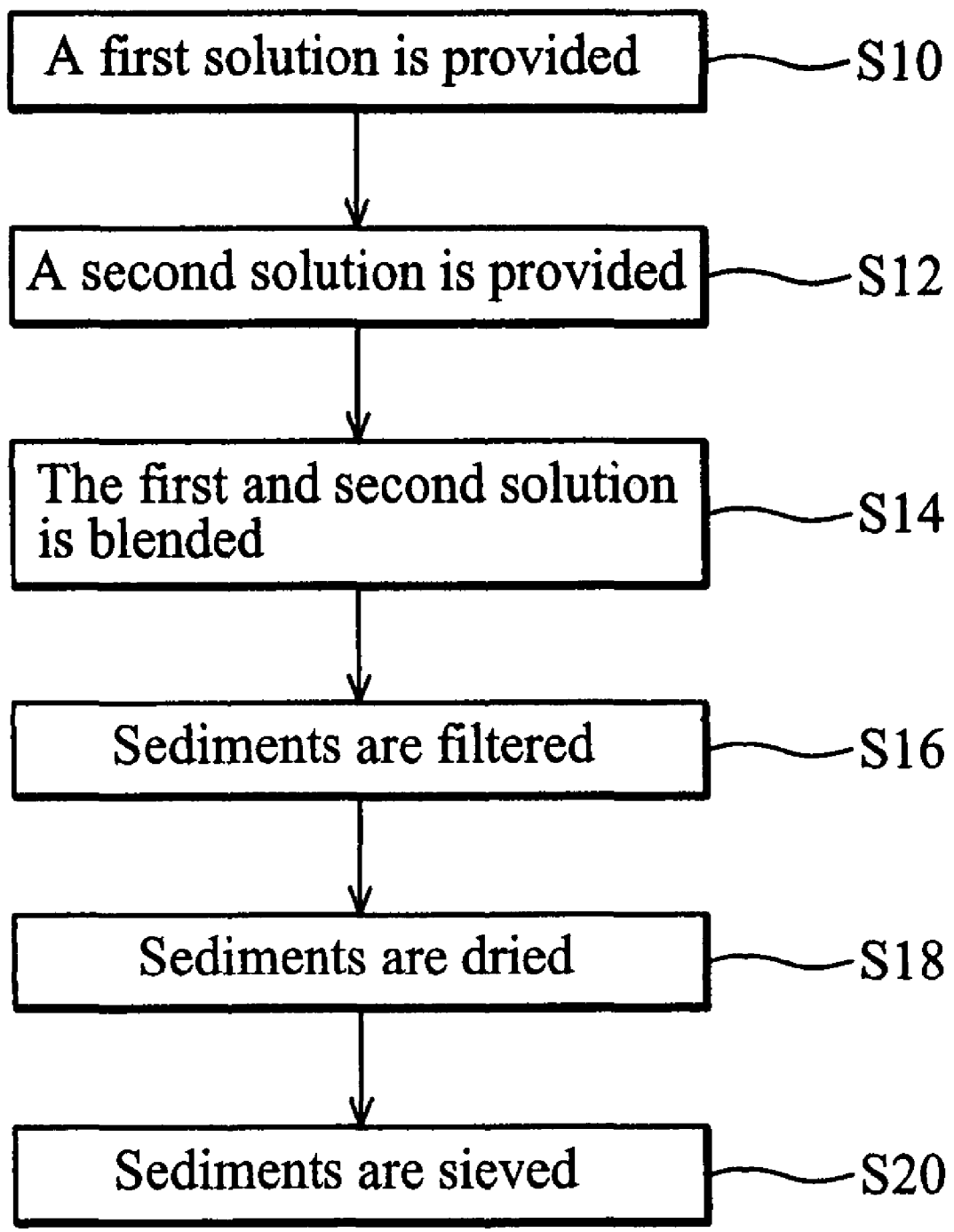
FIG. 1 is a flow chart of the granulating process of the invention.
Figure 2:
FIG. 2 shows the microparticle structure prepared by the invention.

FIG. 1 and FIG. 2 illustrate the method of preparing the taste-masking oral dosage form according to the embodiment of the invention. First, referring to FIG. 1, a first solution is provided in step S10. The first solution comprises solute comprising a pharmaceutically active ingredient and a starch and solvent comprising water or ethanol, wherein the pharmaceutically active ingredient comprises any optional orally administrated drugs, and the starch comprises amylodextrin, hydroxyethyl starch, hydropropyl starch, carboxymethyl starch, acetylated starch, or phosphorylated starch. The uniform and viscous first solution is prepared by heating after blending.

The pharmaceutically active ingredient may be at least one member selected from the group: (1) vitamins, for example, vitamin A, vitamin D, vitamin E, vitamin $B_1$, vitamin $B_2$, vitamin $B_6$, vitamin $B_{12}$, or vitamin C, minerals, for example, Ca, Mg, Fe, or protein, and amino acid or oligosaccharide and the like.

(2) antipyretic-analgesic-antiinflammatory agents, for example, aspirin, acetaminophen, ethenzamide, ibuprofen, diphenhydramine hydrochloride, dl-chorpheniramine maleate, dihydrocodeine phosphate, noscapine, methylephedrine hydrochloride, phenylpropanolamine hydrochloride, caffeine, serratiopeptidase, lysozyme chloride, tolfenamic acid, mefenamic acid, diclofenac sodium, flufenamic acid, salicylamide, aminopyrine, ketoprofen, indomethacin, bucolome, or pentazocine and the like.

(3) antipsychotic drugs, for example, chlorpromazine, reserpine, chlordiazepoxide, diazepam, imipramine, maprotiline, amphetamine, estazolam, nitrazepam, diazepam, phenobarbital sodium, scopolamine hydrobromide, diphenhydramine hydrochloride, or papaverine hydrochloride and the like.

(4) gastrointestinal function conditioning agents, for example, magnesium carbonate, sodium hydrogen carbonate, magnesium aluminometasilicate, synthetic hydrotalcite, precipitated calcium carbonate, or magnesium oxide and the like.

(5) antitussive-expectorants, for example, chloperastine hydrochloride, dextromethorphan hydrobromide, theophylline, potassium guaiacolsulfonate, guaifenesin, oxytetracycline, triamcinolone acetonide, chlorhexidine hydrochloride, or lidocaine and the like.

(6) antihistamines, for example, diphenhydramine hydrochloride, promethazine, isothipendyl hydrochloride, or dl-chlorpheniramine maleate and the like.

(7) cardiotonics, for example, etilefrine hydrochloride, procainamide hydrochloride, propranolol hydrochloride, pindolol, isosorbide, furosemide, delapril hydrochloride, captopril, hexamethonium bromide, hydralazine hydrochloride, labetalol hydrochloride, or methyldopa and the like.

(8) vasoconstrictors, for example, phenylephrine hydrochloride, carbocromen hydrochloride, molsidomine, verapamil hydrochloride, cinnarizine, dehydrocholic acid, or trepibutone and the like.

(9) antibiotics, for example, cephems, penems, carbapenems, cefalexin, amoxicillin, pivmecillinam hydrochloride, or cefotiam dihydrochloride and the like.

(10) chemotherapeutic drugs, for example, sulfamethizole or thiazosulfone and the like.

(11) antidiabetic agents, for example, tolbutamide or voglibose and the like.

(12) drugs for osteoporosis, for example, ipriflavone and the like.

(13) skeletal muscle relaxants, for example, methocarvamol and the like.

Subsequently, a second solution is provided S12. The second solution comprises solute comprising a hydrophilic polymer and a surfactant and solvent comprising water or ethanol, wherein the hydrophilic polymer comprises PEG, PVP, carbopol, polysaccharide, agar, MC, or HPMC, and the surfactant comprises edible surfactants comprising phospholipid.

Next, the first and second solutions are blended in step S14 and continuously stirred to drop the temperature to lower than room temperature. Sediments comprising a plurality of co-crystal microparticles comprising the pharmaceutically active ingredient and the starch may form after cooling, wherein the pharmaceutically active ingredient is packaged by the starch with the package percentage exceeding 95% to isolate the bitter taste, and the diameter of the microparticle is about 150~360 µm, as shown in FIG. 2. Subsequently, the sediments are filtered in step S16, dried in step S18 and sieved in step S20. The granulating process comprises dry granulating, wet granulating, fluidized bed granulating, or spray granulating.

Figure 3:
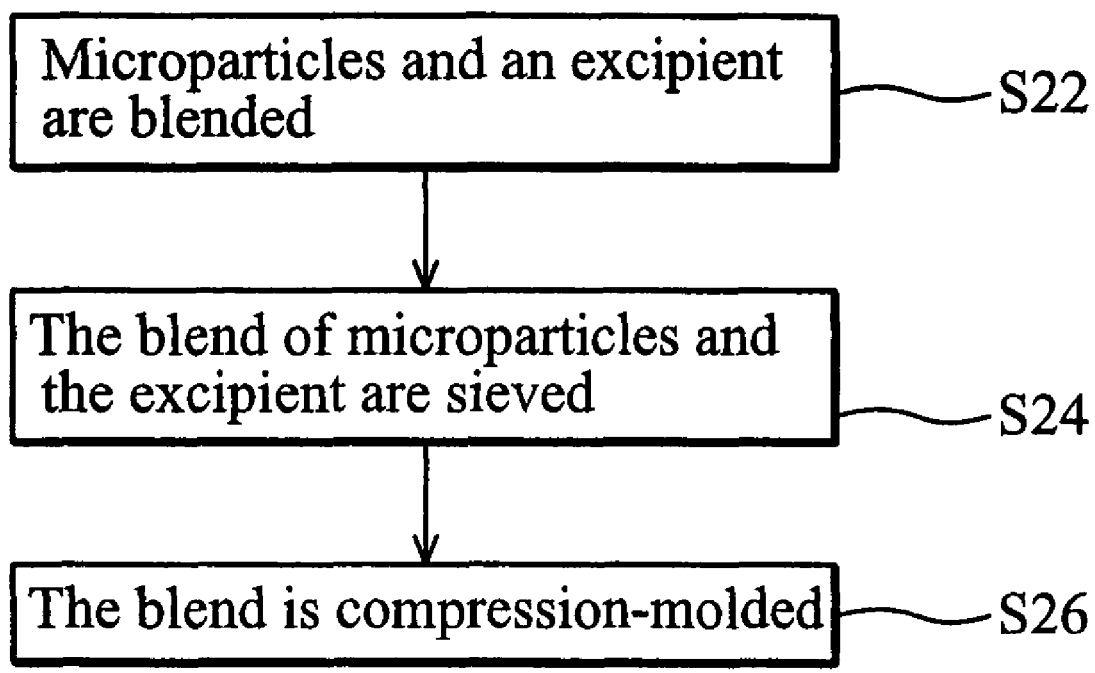
FIG. 3 is a flow chart of the compression-molding process of the invention.

Next, referring to FIG. 3, microparticles and excipients are blended in step S22. The excipients comprises disintegrating agents, effervescent agents, sweeteners, and lubricants comprising saccharide, alcohol, and sugar alcohol, wherein saccharide comprises monosaccharide or disaccharide, and sugar alcohol comprises mannitol, sorbitol, xylitol, or glycerol.

Subsequently, the mixture of microparticles and the excipients is sieved in step S24. After sieving, the mixture is compression-molded in step S26 with a tabletting machine, for example, a High-Speed Rotary Tabletting Machine.

The molding pressure of the High-Speed Rotary Tabletting Machine is about 800~1200 lb/cm$^2$, and preferably 1000 lb/cm$^2$. The molding speed thereof is about 15~20 rpm, and preferably 16 rpm.

The taste-masking oral dosage form of the invention comprises a pharmaceutically active ingredient in a proportion is generally about 35~45% by weight, a starch in a proportion is generally about 20~30% by weight, a hydrophilic polymer in a proportion is generally about 2~10% by weight, a surfactant in a proportion is generally about 2~10% by weight, and excipients in a proportion are generally about 40~50% by weight. Additionally, the porosity of the tablet is about 30~70%, the disintegration time (the time required to complete dissolution by saliva in an oral cavity in a healthy adult male) thereof is less than 1 min, the hardness thereof is about 20~50 NT, and the brittleness thereof is less than 2%. Specifically, the pharmaceutically active ingredient is packaged with starch with the package percentage exceeding 95% to isolate the bitter taste.

Example 1

A first solution comprising acetaminophen (antipyretic-analgesic-antiinflammatory agents), amylodextrin, and $H_2O$ was prepared as described in the following steps. First, 400 g of acetaminophen and 84 g of amylodextrin were added into 1600 ml of $H_2O$, stirred, and the first solution was heated to 90° C.

Subsequently, a second solution comprising a PEG6000 (hydrophilic polymer), lecithin (surfactant), and $H_2O$ was prepared as the following step. First, 50 g of PEG6000 and 50 g of lecithin were added into 790 ml of heated $H_2O$ at 70° C., and stirred to dissolve completely.

Next, a wet granulating process was performed, wherein the first solution was slowly added into the second solution, and continuously stirred to drop the temperature to lower than room temperature during blending. Sediments comprising a plurality of co-crystal microparticles comprising the pharmaceutically active ingredient and the starch was formed after cooling, wherein the pharmaceutically active ingredient is packaged by the starch with the package percentage exceeding 95% to isolate the bitter taste, and the diameter of the microparticle is about 150~360 µm. Subsequently, sediments were filtered through the Buchner funnel, and dried in a dryer at 45° C. Then, sediments were sifted through a sieve with 400 µm diameter mesh.

Next, microparticles and excipients were blended with a V-shaped blender. The excipients comprises 250 g of lactose (disaccharide), 100 g of mannitol (sugar alcohol), and 100 g of crospovidone (disintegrating agents). Subsequently, the blend was sifted through a sieve with 200 µm diameter mesh. Finally, 400 g of the blend was compression-molded to form a tablet with a High-Speed Rotary Tabletting Machine. The molding pressure was about 1000 lb/cm$^2$, and the molding speed was about 15.9 rpm.

In this example, 400 g of acetaminophen in a proportion is generally about 40% by weight, 50 g of amylodextrin in a proportion is generally about 5% by weight, 50 g of PEG6000 in a proportion is generally about 5% by weight, 50 g of lecithin in a proportion is generally about 5% by weight, and 450 g of excipients comprising 250 g of lactose, 100 g of mannitol, and 100 g of crospovidone in a proportion are generally about 25% by weight.

Example 2

To illustrate the effects of the invention in further detail, the following characteristics of the tablets prepared in the foregoing example was determined, comprising disintegration time, hardness, and brittleness. The results are shown in Table 1.

(1) Disintegration Time

The disintegration time of each tablet was determined in accordance with the disintegration test as described in the following. First, 37±2° C., proper amount of water used as solvent was added into the container of the test machine (PHARMA TEST PTZ1 E type). Next, six tablets were added into the container, and the container was covered by a plastic cover. Subsequently, the test machine shook the container until the tablets were disintegrated completely. The mean of the results of six determinations of each pharmaceutically active ingredient was adopted respectively.

(2) Hardness

The hardness of each tablet was determined in accordance with the hardness test as described in the following. First, six tablets were placed on the hardness tester (SHIN KWANG SK-32060 type). Next, pressure was applied from the long axis until the tablets were cracked. The mean of the results of six determinations of each pharmaceutically active ingredient was adopted respectively.

(3) Brittleness

The brittleness of each tablet was determined in accordance with the brittleness test as described in the following. First, 6~6.5 g of sixteen tablets (380~420 mg/per tablet) were placed on the sieve (10 mesh). After dropped powders were removed, the precise sample weight (As) was measured. The sample was then added into the test machine (PHARMA TEST PTFE type), and the test machine spun at a speed of 25 rpm for 100 turns. After the sample was taken out, all dropped powders were removed again. Finally, the precise sample weight (A$_0$) was measured. As a result, Brittleness=(A$_0$/As)* 100. The mean of the results of sixteen determinations of each pharmaceutically active ingredient was adopted respectively.

TABLE 1

| Pharmaceutically active ingredient | Disintegration time(sec) | Hardness (NT) | brittleness (%) |
|---|---|---|---|
| acetaminophen | 20 ± 5 | 24.9 ± 7.0 | 1.2 |

The results of Table 1 indicate that the disintegration time of the oral dosage forms of the present invention is less than 1 min, and the brittleness thereof is less than 2%. Therefore, the elderly, children, or those with impaired swallowing ability are able to swallow the tablets, due to rapid disintegration and absorption in an oral cavity. Additionally, an adequate mechanical strength of 20~50 NT is obtained, facilitating the packaging process in production lines.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of preparing a taste-masking oral dosage form, comprising:
    a. providing a first solution comprising a pharmaceutically active ingredient and a starch;
    b. heating said first solution to about 90° C. to dissolve the pharmaceutically active ingredient and the starch;
    c. providing a second solution comprising a hydrophilic polymer and a surfactant;
    d. blending the first and second solutions with continuous stirring to drop the temperature to lower than room temperature;
    e. precipitating out crystalline microparticles comprising the pharmaceutically active ingredient and the starch, wherein the diameter of said crystalline particles is about 150 to about 360 microns; and
    f. compressing said crystalline microparticles into a tablet having a porosity of about 30% to about 70% and a brittleness of less than 2%.

2. The method as claimed in claim 1, wherein the starch comprises amylodextrin, hydroxyethyl starch, hydropropyl starch, carboxymethyl starch, acetylated starch, or phosphorylated starch.

3. The method as claimed in claim 1, wherein the hydrophilic polymer comprises polyethylene glycol (PEG), polyvinyl pyrrolidone (PVP), carbopol, polysaccharide, agar, methyl cellulose (MC), or hydroxypropyl methyl cellulose (HPMC).

4. The method as claimed in claim 1, wherein the surfactant comprises an edible surfactant.

5. The method as claimed in claim 1, wherein the surfactant comprises lecithin.

6. The method as claimed in claim 1, after the first solution is added into the second solution and blended, an excipient further comprising adding excipients into the blended solution.

7. The method as claimed in claim 6, wherein the excipient comprises disintegrating agents, effervescent, lubricants, or sweeteners.

8. The method as claimed in claim 6, wherein the excipient comprises saccharide, alcohol, or sugar alcohol.

9. The method as claimed in claim 8, wherein saccharide comprises monosaccharide or disaccharide.

10. The method as claimed in claim 8, wherein sugar alcohol comprises mannitol, sorbitol, xylitol, or glycerol.

11. The method as claimed in claim 1, wherein a molding pressure of the compression-molding is about 800 lb/cm² to about.1200 lb/cm².

12. The method as claimed in claim 1, wherein a molding speed of the compression-molding is about 15 rpm to bout 20 rpm.

13. The method as claimed in claim 1, wherein the pharmaceutically active ingredient in a proportion is about 35% to about 45% by weight of the entire tablet.

14. The method as claimed in claim 1, wherein the starch is about 20% to about 30% by weight of the entire tablet.

15. The method as claimed in claim 1, wherein the hydrophilic polymer is about 2% to about 10% by weight of the entire tablet.

16. The method as claimed in claim 1, wherein the surfactant is about 2% to about 10% by weight of the entire tablet.

17. The method as claimed in claim 6, wherein the excipient is about 40% to about 50% by weight of the entire tablet.

18. The method as claimed in claim 1, wherein the solvent of the first solution is water.

* * * * *